United States Patent [19]
Franco et al.

[11] Patent Number: 5,994,414
[45] Date of Patent: Nov. 30, 1999

[54] WATER-THIN EMULSION FORMED BY HIGH PRESSURE HOMOGENIZATION PROCESS

[75] Inventors: Philip Franco, Warwick; Jeffrey Heine, Middletown, both of N.Y.

[73] Assignee: Avon Products, Inc., New York, N.Y.

[21] Appl. No.: 08/847,877

[22] Filed: Apr. 28, 1997

[51] Int. Cl.$^6$ ........................................ A61K 7/00
[52] U.S. Cl. .................... 514/938; 514/512; 514/724; 514/844; 514/845; 514/846; 514/847; 424/401
[58] Field of Search ................ 424/401, 59; 514/724, 514/512, 844, 845, 846, 847, 938

[56] References Cited

U.S. PATENT DOCUMENTS

| | | | |
|---|---|---|---|
| 4,595,586 | 6/1986 | Flom | 424/59 |
| 4,839,163 | 6/1989 | Busch, Jr. | 424/63 |
| 4,892,728 | 1/1990 | Kawa et al. | 424/70 |
| 4,992,476 | 2/1991 | Geria | 514/782 |
| 4,996,004 | 2/1991 | Bucheler et al. | 252/314 |
| 5,010,110 | 4/1991 | Wilmott et al. | 514/758 |
| 5,059,414 | 10/1991 | Dallal et al. | 424/70 |
| 5,116,536 | 5/1992 | Bucheler et al. | 252/314 |
| 5,152,923 | 10/1992 | Weder et al. | 252/312 |
| 5,160,739 | 11/1992 | Kanga | 424/401 |
| 5,384,118 | 1/1995 | La Valle | 424/70.13 |
| 5,496,538 | 3/1996 | Zimmerman et al. | 424/45 |
| 5,525,344 | 6/1996 | Wivell | 424/401 |
| 5,571,503 | 11/1996 | Mausner | 424/59 |
| 5,585,104 | 12/1996 | Ha et al. | 424/401 |

OTHER PUBLICATIONS

What's New In Cosmetic R&D? Carolyn A. Dunn, Happi, Jan. (1996) p. 56.

*Primary Examiner*—Jose' G. Dees
*Assistant Examiner*—Michael A. Williamson
*Attorney, Agent, or Firm*—Ohlandt, Greeley, Ruggiero & Perle, LLP

[57] ABSTRACT

A stable, water-thin emulsion is formed by processing a crude emulsion through a high pressure homogenizer at a pressure of about 900 to about 1100 bar. This emulsion contains low levels of emulsifier and contains no post addition stabilizers.

14 Claims, No Drawings

WATER-THIN EMULSION FORMED BY HIGH PRESSURE HOMOGENIZATION PROCESS

FIELD OF THE INVENTION

The present invention concerns a stable oil-in-water emulsion formed by a high pressure homogenization process. More particularly, this water-thin emulsion requires no stabilizing gums or thickeners, and preferably contains only low levels of emulsifiers.

BACKGROUND OF THE INVENTION

Emulsions that have been homogenized are known in the art. They typically require stabilizing gums or thickeners to maintain the stability of the discrete oil phase within the continuous water phase. The type and concentration of emulsifiers, as well as the viscosity of the emulsion, influence the overall stability of the emulsion. Standard propeller-type mixers or standard homogenizers are typically used to manufacture emulsions.

Emulsions made by high pressure homogenization are also known. These emulsions can range from thick, non-flowing creams to light lotions. The light lotions typically require a post addition after high pressure homogenization of a gum or thickener to stabilize the emulsion.

U.S. Pat. No. 4,996,004 to Bucheler et al. provides, in its discussion of the prior art, the formation of cosmetic emulsions by combining heated oily and aqueous phases, cooling the mixture and dispersing it in a "high-pressure" homogenizer at levels of about 200 bar [col. 1, lines 19–44]. However, no suggestion is made that thickeners or gums can be eliminated, or that lower levels of emulsifiers are effective.

U.S. Pat. No. 5,152,923 to Weder et al. provides a process for producing a stable nanoemulsion of oil particles, specifically triglyceride or fatty acid esters, in a water phase using 0.1 to 0.4 parts by weight of a lecithin-type amphoteric emulsifier. The emulsifier forms a lamellar liquid-crystalline structure in the aqueous phase. The mixture is then processed into a nanoemulsion in a high-pressure homogenizer, at pressures of 500 to 1000 bar. Moreover, tests have shown that emulsions formed with the emulsifiers taught by this patent are viscous, and are unstable at elevated temperatures.

SUMMARY OF THE INVENTION

Accordingly, it is an object of the present invention to provide a stable, water-thin (having essentially the consistency of water) lotion that is suitable as a spray-on lotion.

It is a further object of the present invention to provide a high pressure homogenized emulsion that requires no thickening or stabilizing agents.

It is a still further object of the present invention to provide an emulsion that requires low levels of emulsifiers.

It is a further object of the present invention to provide a more cosmetically acceptable lotion having no irritating thickening or stabilizing agents, and a minimum of emulsifiers.

The high pressure homogenized emulsions of the present invention are stable, water-thin lotions that require no stabilizing gums or thickeners, and low levels of emulsifiers.

DESCRIPTION OF THE PREFERRED EMBODIMENTS

The lotions or other emulsified products of the present invention are stable lotions that require no stabilizing gums or thickeners, and only low levels of emulsifiers. By stable, it is meant that the emulsions of the present invention do not separate under normal or more extreme conditions. While some emulsions are "stable" at room temperature only, the emulsions of the present invention are stable at elevated temperatures (such as may be experienced during shipping or storage), over long time spans.

The preferred embodiment is manufactured as a concentrated pre-mix which is then incorporated into a fragranced and colored water base. Most preferably, non-ionic emulsifiers are used. Based on the instability of the emulsion taught by the Weder et al. patent, it is believed that non-amphoteric and non-lecithin type emulsifiers are preferred for use in the present invention.

The high pressure homogenization process of the present invention is the conveyance of a crude oil-in-water emulsion (mean particle size of about 0.5–3.0 microns) into a high pressure device, where the emulsion is subjected to very high pressures, preferably on the order of about 900 to about 1100 bar, more preferably about 1000 to about 1100 bar. The preferred operating pressure is dependent on the type and concentration of emulsifier used. When less emulsifier is used, the high pressure homogenization must be performed at higher pressure settings. Conversely, when higher levels of emulsifier (although still low levels) are used, the range of preferred pressure settings is broadened. The mean particle size of the resulting product is about 0.1 microns, with a maximum particle size of about 1 micron.

A preferred lotion according to the present invention is formulated in two steps. First, a lotion pre-mix is formed. This pre-mix is preferably of the following formula:

|  | Weight Percent |
|---|---|
| Part A | |
| Demineralized Water | 31.68 |
| Disodium EDTA | 0.20 |
| Glycerin | 10.00 |
| Part B | |
| Ethylhexyl palmitate | 20.00 |
| Stearyl ETO (20M) alcohol | 1.20 |
| POE (2M) stearyl alcohol | 0.72 |
| POE fatty alcohols | 2.00 |
| Glyceryl monostearate-acid stable | 1.40 |
| Methyl paraben | 0.40 |
| Part C | |
| Demineralized Water | 30.00 |
| Part D | |
| Demineralized Water | 2.00 |
| Imidazolidinyl Urea | 0.40 |

Of the foregoing ingredients, ethoxylates of stearyl alcohol, such as stearyl ETO (20M) alcohol and POE (2M) stearyl alcohol, are the emulsifiers most preferred for use in the present invention. Also preferred for use in the lotions of the present invention are ethoxylated hydrogenated castor oil emulsifiers.

This preferred pre-mix is then incorporated into a lotion of the following composition.

| | |
|---|---|
| Part 1 | 50.00 |
| Pre-mix (above) | |
| Part 2 | 0.15 |
| Fragrance | |

-continued

| | |
|---|---|
| Part 3 Demineralized water | 49.837 |
| Part 4 FD & C dyes | 0.013 |

In formulating this lotion, the following processing procedure is preferably employed. All equipment is cleaned and sanitized. The Part B ingredients are loaded into a batch tank equipped with propeller agitation and a mill. The Part B ingredients are heated to about 160 to about 165° F. Medium speed agitation is maintained. Mixing continues at about 160 to about 165° F. for about fifteen minutes and until all ingredients have fully melted.

The Part A demineralized water is loaded into a side kettle equipped with propeller agitation. The remaining Part A ingredients are added to the side kettle and are heated to about 140 to about 145° F. The mixture is mixed at about 140 to about 145° F. until all solids have dissolved.

With both phases, Part A and Part B, at the specified temperatures, Part A is slowly transferred through filter cloth into Part B with medium speed mixing and milling. The addition preferably takes about 15 to about 20 minutes. The emulsion must go through a true inversion. The batch is mixed and milled for about 15 to about 20 minutes following the transfer.

Following the mixing period, the Part C demineralized water is slowly added to the batch. Then, the batch is cooled to about 110 to about 115° F. Medium speed mixing is maintained during cooling.

The Part D ingredients are combined in a suitable container and are mixed until a complete solution is obtained. Once the batch temperature has dropped below about 115° F., Part D is added with medium speed mixing. The batch continues to be cooled, to about 85 to about 90° F.

Once the batch temperature has dropped below about 90° F., mixing is stopped. It is preferred that the resulting pre-mix be processed into a finished lotion within about 96 hours.

The pre-mix is then transferred through the high pressure homogenizer, preferably at about 1000 to about 1100 bar. The heat exchanger on the exit side of the homogenizer is set to give a product outlet temperature below 100° F. Samples can be withdrawn from the beginning, middle and end of the transfer for analysis.

The lotion is then formulated according to the following process. The homogenized pre-mix (Part 1) is transferred into a mixing tank equipped with propeller agitation, and medium to fast speed mixing is initiated. The Part 2 fragrance is then added to Part 1. Mixing is continued for about 15 to about 20 minutes and until the fragrance has been completely incorporated.

The Part 3 demineralized water is then added to the mixing tank. The Part 4 color solution is then added to the mixing tank. The batch is mixed for about 15 to about 20 minutes and until uniform. Once uniform, mixing is stopped. The batch can then be transferred to a filler machine or into suitable storage containers. This water-thin lotion is suitable for distribution in a spray bottle. The lotion can be misted onto the skin and rubbed in by the user.

This lotion is stable over normal temperatures and pressures encountered during delivery, storage and use, without the use of gums or thickeners. Moreover, the lotion retains its stability over time. In fact, lotions having the preferred formulation set forth above have been found to be stable under very severe conditions. Specifically, the emulsions have remained stable even after being held at temperatures of up to 140° F. for four weeks.

These water-thin emulsions can have essentially no viscosity. They will stay in a stable dispersed state with essentially no coalescing—formation of larger oil particles—that would cause the lotion to destabilize, become less cosmetically acceptable or clog the dispenser.

The lotions and processes of the present invention have several advantages. Because thickeners and gums can be eliminated, and because emulsifier content is lowered, the lotions are able to be produced at reduced cost. For the same reasons, the lotions produced have improved skin mildness. Moreover, these fine emulsions provide quicker availability of skin treatment ingredients carried therein, and have a non-greasy afterfeel. In addition to a spray-on lotion, another preferred use of lotions of the present invention is in roll-on deodorants and anti-perspirants, where a water-thin emulsion is particularly suitable. Once the stable water-thin emulsion of the present invention is formed, it may subsequently be modified to provide a viscosity or other characteristics suitable for use in a desired end-product.

A preferred roll-on antiperspirant lotion formula pre-mix made according to the process of the present invention has the following formula:

| Pre-Mix | Weight Percent (of total) |
|---|---|
| POP (15M) stearyl ether | 1.00 |
| Isopropyl palmitate | 0.50 |
| Dicapryl adipate | 1.00 |
| POE (7M) hydrogenated castor oil | 1.18 |
| POE (40M) hydrogenated castor oil | 0.57 |
| Methyl paraben | 0.20 |

The roll-on pre-mix is then processed through the high pressure homogenizer, as set forth above, and incorporated into the finished product according to the process generally set forth above. The finished product consists of:

| | |
|---|---|
| Demineralized water | 60.15 |
| Pre-mix | 4.45 (see above) |
| Fragrance | 0.40 |
| Aluminum chlorohydrate | 35.00 |

Of the foregoing ingredients, the ethoxylated hydrogenated castor oil emulsifiers are the preferred emulsifiers. Another preferred formulation can include 0.944 weight percent POE (7M) hydrogenated castor oil and 0.456 weight percent POE (40M) hydrogenated castor oil. The amount of demineralized water used in the final product is adjusted accordingly.

In the alternative, other emulsifiers useful in this formulation include stearyl ETO (20M) alcohol and POE (2M) stearyl alcohol (for example at 0.50 and 0.20 weight percent, respectively, or at 0.75 and 0.30 weight percent, respectively, with the water content adjusted accordingly).

The lotions of the present invention can accommodate variations in the concentration of ingredients. It is known that the preferred lotion formulation set forth above can tolerate at the very least about five percent increases and decreases in the weight percent of the individual ingredients, as based on the preferred weight percent set forth. It is believed that much broader ranges are acceptable.

A preferred range of emulsifier is about 0.5 to about 2 weight percent emulsifier (based on the total weight of the emulsion). This low level of emulsifier is all that is necessary in the emulsions of the present invention. Larger proportions of emulsifiers can be used, but are not needed. It is known that up to about a forty percent increase or decrease in the amount of emulsifiers can be used successfully in the preferred lotion formulations set forth above. Moreover, the minimum amount of emulsifier needed will vary, depending on the particular composition and the emulsifier or emulsifiers selected. Any amount of emulsifier, water and oil that forms a stable emulsion without thickeners or gums when processed under high speed homogenization according to the present invention should be considered to fall within the purview of this invention.

Various modifications may be made to the processes and emulsions of the present invention, as will be apparent to those skilled in the art. Thus, it will be obvious to one of ordinary skill in the art that the foregoing description is merely illustrative of certain preferred embodiments of the present invention, and that various obvious modifications can be made to these embodiments.

What is claimed is:

1. A stable, water-thin emulsion that is formed by processing a crude emulsion through a high pressure homogenizer at a pressure of about 900 to about 1100 bar, said crude emulsion comprising an emulsifier, and having a mean particle size of about 0.1 microns, wherein said emulsifier is not lecithin or a lecithin derivative and the stable, water-thin emulsion is free of stabilizing gums or thickeners and is stable at temperatures up to 140° F.

2. The water-thin emulsion of claim 1, wherein said crude emulsion is an oil-in-water emulsion.

3. The water-thin emulsion of claim 1, wherein said emulsifier is non-ionic.

4. The water-thin emulsion of claim 1, wherein said emulsifier is non-amphoteric.

5. The water-thin emulsion of claim 1, wherein said emulsifier is present at a low level.

6. The water-thin emulsion of claim 5, wherein said emulsifier is present from about 0.50 to about 2 percent by weight of said water-thin emulsion.

7. The water-thin emulsion of claim 1, wherein said emulsifier is an ethoxylate of stearyl alcohol.

8. The water-thin emulsion of claim 1, wherein said emulsifier is an ethoxylated hydrogenated castor oil.

9. The water-thin emulsion of claim 1, wherein said water-thin emulsion has a maximum particle size of about one micron.

10. The stable, water-thin emulsion of claim 1, wherein said emulsifier is selected from the group consisting of ethoxylates of stearyl alcohol and ethoxylated hydrogenated castor oil emulsifiers.

11. A stable, water-thin emulsion that is formed by processing a crude emulsion through a high pressure homogenizer at a pressure of about 900 to about 1100 bar, wherein the water-thin emulsion comprising an emulsifier and having a mean particle size of about 0.1 microms, wherein the emulsifier is not lecithin or a lecithin derivative and the stable water-thin emulsion is free of stablizing gums or thickeners is stable at about 140° F. for about four weeks.

12. A process of forming a stable, water-thin emulsion, comprising:

forming a crude oil-in-water emulsion, said crude oil-in-water emulsion containing an emulsifier; and processing said crude oil-in-water emulsion through a high pressure homogenizer at a pressure from about 900 to about 1100 bar to obtain a mean particle size of about 0.1 microns, wherein said emulsifier is not lecithin or a lecithin derivative, and the stable, water-thin emulsion is free of stabilizing gums or thickeners and is stable at temperatures up to 140° F.

13. The process of claim 12, wherein said crude oil-in-water emulsion is maintained at less than about 100° F. during processing through said high pressure homogenizer.

14. The process of claim 12, wherein said wherein said emulsifier is selected from the group consisting of ethoxylates of stearyl alcohol and ethoxylated hydrogenated castor oil emulsifiers.

* * * * *